United States Patent
Tu et al.

(10) Patent No.: US 6,241,727 B1
(45) Date of Patent: Jun. 5, 2001

(54) ABLATION CATHETER SYSTEM HAVING CIRCULAR LESION CAPABILITIES

(75) Inventors: Hosheng Tu; Cary Hata, both of Tustin, CA (US)

(73) Assignee: Irvine Biomedical, Inc., Irvine, CA (US)

( * ) Notice: Subject to any disclaimer, the term of this patent is extended or adjusted under 35 U.S.C. 154(b) by 0 days.

(21) Appl. No.: 09/351,080

(22) Filed: Jul. 9, 1999

Related U.S. Application Data

(63) Continuation-in-part of application No. 09/085,543, filed on May 27, 1998, now abandoned.

(51) Int. Cl.$^7$ ................................................ A61B 18/18
(52) U.S. Cl. ........................ 606/41; 606/27; 607/101
(58) Field of Search ........................... 606/27–31, 41, 606/42, 45, 48–50; 607/101, 102

(56) References Cited

U.S. PATENT DOCUMENTS

| | | | |
|---|---|---|---|
| 5,191,883 | * 3/1993 | Lennox et al. | 606/27 |
| 5,840,076 | 11/1998 | Swanson et al. | 606/34 |
| 5,891,134 | * 4/1999 | Goble et al. | 606/27 |
| 5,921,983 | * 7/1999 | Shannon, Jr. | 606/45 |
| 6,071,277 | * 6/2000 | Farley et al. | 606/27 |

OTHER PUBLICATIONS

Lesh MD et al. "Novel Technology for Catheter Ablative Cure of Atrial Fibrillation", Submitted for Journal of Cardiovascular Electrophysiology 1999.

* cited by examiner

Primary Examiner—Michael Peffley

(57) ABSTRACT

An improved catheter system having a movable bipolar electrode pair means enclosed within an inflatable balloon capable of treating a tissue of a patient. In one embodiment, a catheter suitable for radiofrequency ablation of cardiac tissues comprises an electrode means having a first movable electrode positioned at an elongated open groove and a second electrode to form a bipolar electrode pair, wherein the electrode means is mounted at a shaft distal tip section and is completely enclosed within the inflatable balloon. RF energy is delivered to the first electrode through a first electrical conducting means, transmitted from the first electrode to the second electrode, and returned from the second electrode to said generator means through a second electrical conducting means for generating heat uniformly inside the inflatable balloon.

13 Claims, 6 Drawing Sheets

US 6,241,727 B1

ABLATION CATHETER SYSTEM HAVING CIRCULAR LESION CAPABILITIES

CROSS-REFERENCE TO RELATED APPLICATIONS

This application is a continuation-in-part of application Ser. No. 09/085,543, filed May 27, 1998, now abandoned. It is incorporated herein by reference.

FIELD OF THE INVENTION

The present invention generally relates to improved constructions and methods for a catheter system. More particularly, this invention relates to a catheter system and methods for ablating tissues via a steerable ablation catheter comprising a bipolar electrode pair means within an inflatable balloon for heating the fluid medium, which has circular lesion capabilities.

BACKGROUND OF THE INVENTION

The heart includes a number of normal pathways that are responsible for the propagation of electrical signals from the upper chamber to the lower chamber necessary for performing normal systole and diastole function. The presence of an arrhythmogenic site or accessory pathway can bypass or short circuit the normal pathway, potentially resulting in very rapid heart contractions, referred to herein as tachycardias.

A variety of approaches, including drugs, implantable pacemakers/defibrillators, surgery, and catheter ablation have been proposed to treat tachycardias. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter tip to the exact site for ablation. Once at the site, it is important for a physician to control the emission of energy to ablate the tissue within or around the heart.

Of particular interest to the present invention are radiofrequency (RF) ablation protocols that have been proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablations tip electrode lies exactly at the target tissue site. Radiofrequency energy or other suitable energy is then applied through the tip electrode to the cardiac tissue in order to ablate the tissue of the arrhythmogenic site or the accessory pathway. By successfully destroying that tissue, the abnormal signal patterns responsible for the tachycardia may be eliminated. However, in the case of atrial fibrillation (AFib) or atrial flutter, multiple arrhythmogenic sites and/or multiple accessory pathways exist. The conventional catheter with a single "stationary" ablation electrode can not effectively cure the symptoms. In the case of paroxysmal atrial fibrillation, a circular lesion at about the pulmonary vein is required.

Atrial fibrillation is believed to be the result of the simultaneous occurrence of multiple wavelets of functional re-entry of electrical impulses within the atria, resulting in a condition in which the transmission of electrical activity becomes so disorganized that the atria contracts irregularly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year are AFib-related.

A catheter utilized in the endocardial RF ablation is inserted into a major vein or artery, usually in the neck or groin area. For paroxysmal AFib indications, a catheter is approached from the atrium to the ostium of a pulmonary vein. The tip section of a catheter is referred to here as the portion of that catheter shaft containing means for thermal lesion which may be deflectable and may be adapted to form a circular or an irregular-shape loop lesion. The means for circular thermal lesion is to be positioned against the ostium of the pulmonary vein, whereby the circular ablation means having a firm element, such as a heated inflatable balloon, can be pressed against the tissue for circular ablation.

The tip section of a conventional electrophysiology catheter that is deflectable usually contains one large electrode about 4 to 8 mm in length for ablation purposes. Sometimes, a plurality of long electrodes is used in creating a contiguous linear lesion. However, for creating a circular lesion with uniform lesion quality, the temperatures at various device-to-tissue contact sites should be as uniform as possible. A catheter with a heated balloon has been widely used to apply heat to the balloon-to-tissue sites. The temperature of the fluid medium inside an inflated balloon is far from uniform because the heat source and fluid medium are stationary having poor heat transfer property.

Avitall in the U.S. Pat. No. 5,242,441 teaches a rotatable tip electrode. Said electrode is secured to a high torque wire for rotation and electrical conductivity. The tissue contact site is always the same spot even the electrode is rotated. Moreover, a movable band electrode has been recently introduced to the market to simulate the "rollable electrode" concept. Since the said band electrode does not roll, the contact surface spot of the said band electrode with tissues is always the same spot. The potential coagulum at the contact electrode surface spot due to impedance and temperature rises, would not go away because of its relatively stationary position of the rotatable tip electrode or the movable band electrode.

U.S. Pat. No. 5,840,076 discloses a balloon type electrode catheter by using balloon as a medium to create a circular lesion, wherein the balloon is made of a porous material. Said patent discloses a RF circuit by including a patient in the circuit loop, whereby the heat generated by the uni-polar RF current at the tissue contact site may unexpectedly hurt the patient. The local fixed heat source of the uni-polar means may make the temperature of the fluid inside and around the heated balloon non-uniform. The temperature at the heat source is highest whereas the heat can spread to different regions of the fluid of the inflated balloon when a movable heat source is used.

While a radiofrequency electrophysiology ablation procedure using an existing balloon catheter has had promising results, the temperature at the balloon periphery should be uniform so that a uniform circular lesion can be created for the paroxysmal AFib at a pulmonary vein. Therefore there is a need for an improved catheter and methods for making a circular lesion in the cardiac tissue employing a balloon-type thermal ablation with a bipolar electrode pair means within an inflated balloon.

SUMMARY OF THE INVENTION

In general, it is an object of the present invention to provide a movable bipolar electrode means to a catheter. The "movable electrode" is defined in this invention as the electrode that is slidable or rollable in the axial direction with respect to the catheter shaft itself. A catheter with a movable electrode means is disclosed U.S. Pat. No. 5,843, 152 and U.S. Pat. No. 5,893,884, which is incorporated herein by reference.

It is another object to provide a catheter having a bipolar electrode means enclosed within an inflatable balloon to generate uniform heat to the balloon wall for circular lesion purposes. It is still another object to provide a catheter having a movable bipolar electrode means enclosed within an inflatable balloon to generate uniform heat for circular lesion purposes.

In one embodiment, an ablation catheter system comprises a flexible catheter shaft having a shaft distal tip section, a shaft distal end, a shaft proximal end, and at least one lumen extending therebetween. The shaft distal tip section has an elongated open groove, wherein the at least one lumen comprises an inflation lumen. A handle is attached to the shaft proximal end, wherein the handle has a cavity. An inflatable balloon is mounted at the shaft distal tip section, wherein the inflation lumen opens into and is in communication with an interior of the inflatable balloon. The ablation catheter system further comprises an electrode means comprising a first movable electrode positioned at the elongated open groove and a second electrode to form a bipolar electrode pair, wherein the electrode means is mounted at the shaft distal tip section and is completely enclosed within the inflatable balloon; and an electrode deployment means mounted on the handle for longitudinally moving the first movable electrode of the electrode means back and forth along the elongated open groove.

In a preferred embodiment, the electrode means may further comprise a support and an anchoring leg means disposed inside the elongated open groove for the movable electrode, wherein said movable electrode is positioned on the support and wherein the support is connected to the anchoring leg means which is then secured onto a moving wire means of the electrode deployment means. In a further embodiment, the second electrode may be positioned on a second support and wherein the second support is connected to a second anchoring leg means which is then secured onto said moving wire means of the electrode deployment means.

The inflatable balloon may be made of a material selected from the group consisting of silicone, polyurethane, polyethylene, cross-linked polyethylene, conductive silicone, polyethylene terephthalate, latex, semi-permeable membrane, and nylon. And a sodium chloride containing liquid may be used to inflate the inflatable balloon. The concentration of sodium chloride is preferably appropriate for conducting RF energy from the first electrode to the second electrode to generate heat within the inflatable balloon.

The ablation catheter further comprises a steering mechanism at the handle for controlling deflection of said shaft distal tip section. Usually a rotating ring or a push-pull plunger is employed in the steering mechanism. In another embodiment, the steerable ablation catheter comprises a bidirectional deflection or multiple curves deflection of the tip section. One end of the steering wire is attached at certain point of the tip section of the said catheter shaft. The other end is attached to the steering mechanism at the handle. The steering mechanism on a steerable catheter or device is well known to those who are skilled in the art.

The catheter system further comprises a RF energy generator means, wherein RF energy is delivered to the first electrode through a first electrical conducting means, transmitted from the first electrode to the second electrode, and returned from the second electrode to said generator means through a second electrical conducting means for generating heat inside the inflatable balloon. The bipolar electrode pair is made of a material selected from the group consisting of platinum, iridium, gold, silver, stainless steel, and Nitinol. In another embodiment, the surface area of the electrode pair is variable to enable differing heating profiles of the fluid within the inflatable balloon. The surface area of either electrode can range from 3 $mm^2$ to 100 $mm^2$.

In a particular embodiment, at least one other electrode is disposed at the distal tip section of the catheter shaft. One conducting wire which is soldered to said electrode passes through the lumen of the catheter shaft and the interior void of the handle and is thereafter soldered to a contact pin of the connector secured at the proximal end of the handle. Therefrom, the conducting wire is connected to an EKG monitor for recording and displaying of the endocardial or epicardial electrical signal from the electrode.

In another preferred embodiment, a tissue ablation catheter system comprises a flexible catheter shaft having a shaft distal tip section, a shaft distal end, a shaft proximal end, and at least one lumen extending therebetween, wherein the at least one lumen comprises an inflation lumen. A handle is attached to the shaft proximal end, wherein the handle has a cavity. An inflatable balloon is mounted at the shaft distal tip section, wherein the inflation lumen opens into and is in communication with an interior of the inflatable balloon. The tissue ablation catheter system further comprises an electrode means comprising a first electrode and a second electrode to form a bipolar electrode pair, wherein the electrode means is mounted at the shaft distal tip section and is completely enclosed within the inflatable balloon; and a RF energy generating means, wherein RF energy is delivered to the first electrode through a first electrical conducting means, transmitted from the first electrode to the second electrode, and returned from the second electrode to said generator means through a second electrical conducting means for generating heat inside the inflatable balloon for tissue ablation.

A method for operating a catheter system having a bipolar electrode pair enclosed within an inflatable balloon within a heart, the method may comprise (a) percutaneously introducing the catheter system through a blood vessel to the heart; (b) positioning the shaft distal tip section on an interior wall of the heart; and (c) applying RF energy to the bipolar electrode pair for tissue ablation, wherein RF energy is provided from an external RF energy generator means to the first electrode through a first electrical conducting means, transmitted from the first electrode to the second electrode, and returned from the second electrode to said generator means through a second electrical conducting means for generating heat inside the inflatable balloon.

The catheter system of the present invention has several significant advantages over known catheters or ablation techniques. In particular, the bipolar electrode pair means within an inflatable balloon as a heating source of this invention may result in a uniform circular lesion that is highly desirable in paroxysmal atrial fibrillation treatments.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
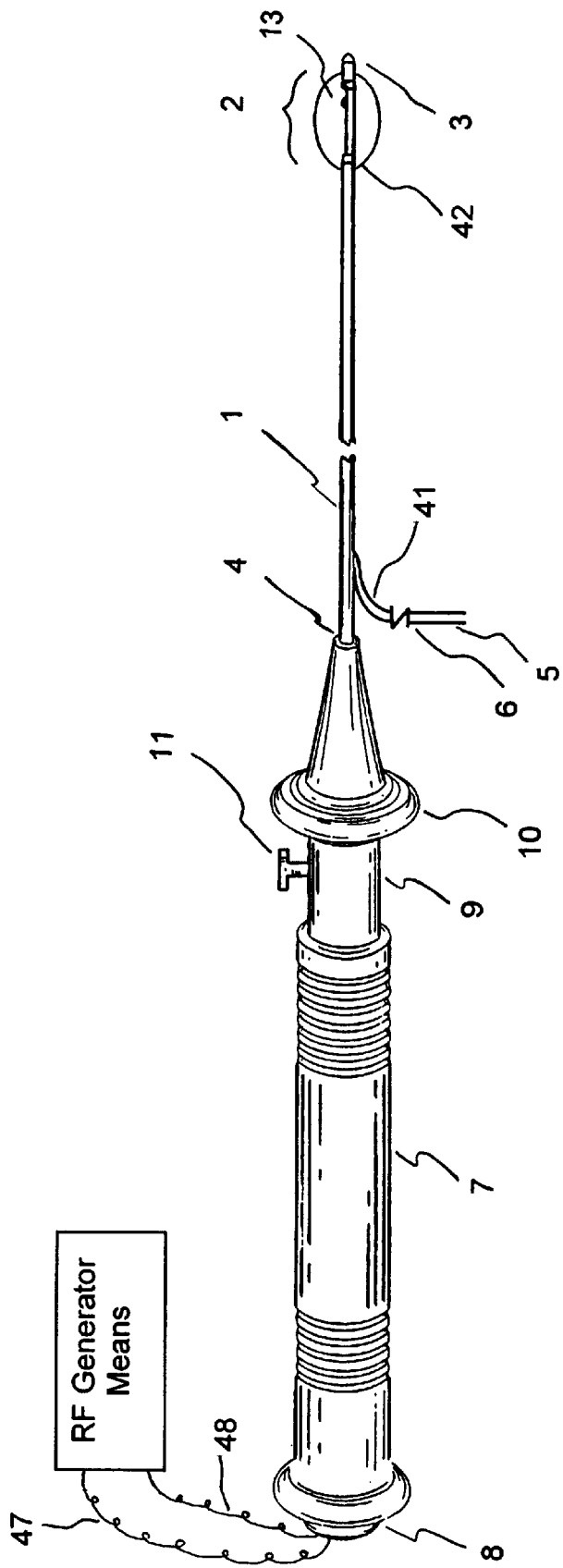
FIG. 1 is an overall view of a catheter system having a bipolar electrode pair means enclosed within an inflatable balloon at its distal tip section constructed in accordance with the principles of the present invention.

FIG. 1 shows an overall view of the catheter system having a bipolar electrode pair means at its distal tip section. A catheter system constructed in accordance with the principles of the present invention comprises a flexible catheter shaft 1 having a shaft distal tip section 2, a shaft distal end 3, a shaft proximal end 4, and at least one lumen extending therebetween, wherein the at least one lumen comprises an inflation lumen 41. A handle 7 is attached to the proximal end 4 of the said catheter shaft 1.

A connector 8 secured at the proximal end of the catheter system, is part of the handle section 7. The handle has one optional steering mechanism 9. The steering mechanism 9 is to deflect the tip section 2 of the catheter shaft 1 for catheter maneuvering and positioning. By pushing forward the front plunger 10 of the handle 7, the distal tip section 2 of the catheter shaft deflects to one direction. By pulling back the front plunger 10, the tip section returns to its neutral position. In another embodiment, the steering mechanism 9 at the handle 7 comprises means for providing a plurality of deflectable curves on the distal tip section 2 of the catheter shaft 1. The mechanism of an ablation catheter having multiple flexible curves is described by a patent application Ser. No. 08/763,614, now U.S. Pat. No. 5,782,828, which is incorporated herein by reference.

In a preferred embodiment, the catheter system comprises an inflatable balloon 42 mounted at the shaft distal tip section 2. The catheter system further comprises a fluid inflation mechanism 5 close to the proximal end 4 of the catheter shaft 1. A control valve 6 is provided to the fluid inflation mechanism 5 which is externally connected to a fluid supply source having a syringe or pump for inflating the inflatable balloon 42. The inflation lumen 41 opens into and is in communication with an interior 43 of the inflatable balloon 42.

Figure 2:
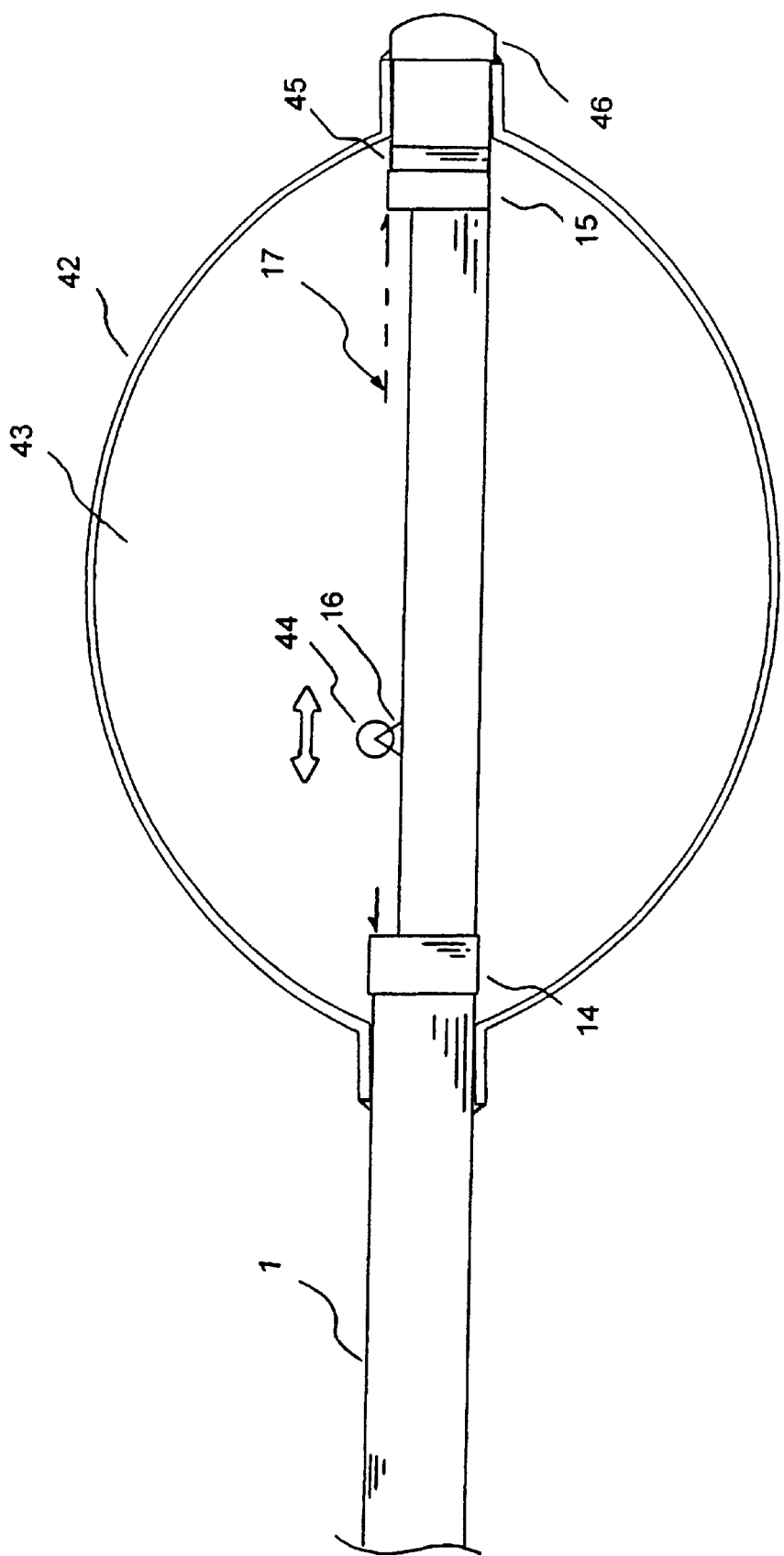
FIG. 2 is a close-up view of the distal section of the catheter system comprising a movable electrode means at the distal end having linear lesion capabilities.

FIG. 2 shows a close-up view of the distal section of the catheter system comprising a movable electrode means 13 enclosed within an inflatable balloon 42 at the shaft distal tip section 2. In one embodiment, the catheter system has an electrode means 13, which comprises a first movable electrode 44 positioned about the elongated open groove and a second electrode 45. The first electrode 44 and the second electrode 45 form a bipolar electrode pair.

An electrode deployment means 11 is mounted on the handle 7, wherein a moving wire 12 (shown in FIG. 3) is secured to the electrode deployment means 11 and is capable of longitudinally moving the first electrode 44 forward and backward along the elongated open groove 17. A first electrode 44 is disposed and secured on the moving wire 12 so that the rollable electrode is controlled back and forth by the said electrode deployment 11. The range of the movable electrode 13 at the distal tip section 2 is restricted by a first stopper 14 and a second stopper 15. The first stopper and the second stopper are made of non-conductive material.

The electrode means 13 further comprises a support 16 and an anchoring leg means 19 disposed inside the elongated open groove 17 for the movable electrode 44, wherein said movable electrode is positioned on the support and wherein the support is connected to the anchoring leg means which is then secured onto a moving wire means 12 of the electrode deployment means 11.

Figure 3:
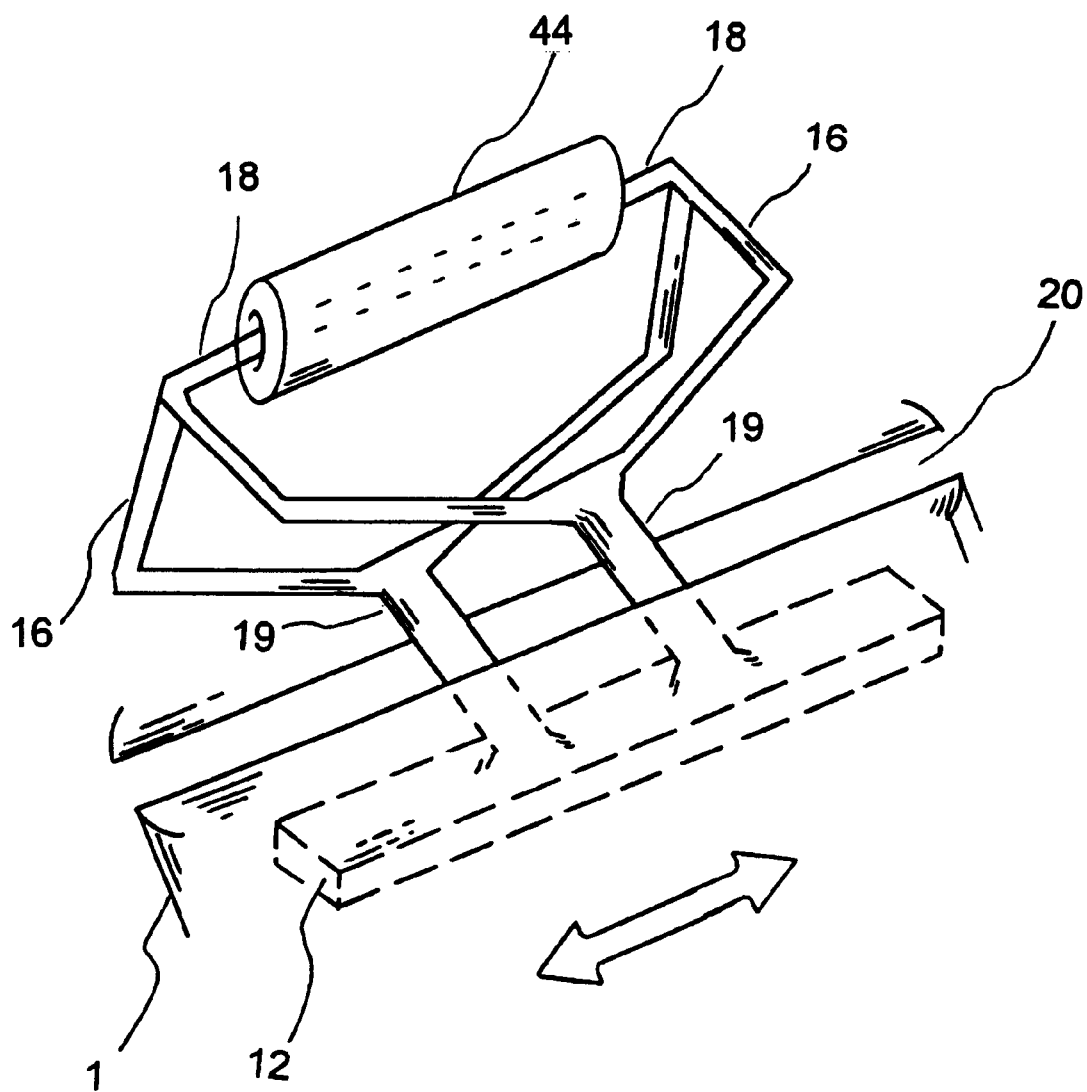
FIG. 3 is a perspective view of the electrode element, including a movable electrode at the distal section of a catheter system.

FIG. 3 shows a perspective view of the electrode element 13, including a movable or rollable electrode 44 at the distal section 2 of the catheter system. The first electrode 44 of the bipolar electrode pair consists of a rollable electrode 13, a pair of electrode shafts 18, a plurality of supports 16, and an anchoring leg means 19. Said electrode may be selected from a group consisting of a cylindrical roller, a ball-type roller, an oval-type roller, a porous roller, a roller with studded surface and the like. The first electrode 44 and the second electrode 45 is preferably made of conductive material, while the surfaces of the shafts 18, supports 16, the anchoring leg means 19, and the moving wire 12 are preferably covered with an insulating material or insulated. The anchoring leg means 19 is secured to the moving wire 12 through an open slit 20 of the open groove 17, wherein the moving wire 12 is preferred to be made of a flat wire. When the moving wire is pushed forward by the electrode deployment means 11, the rollable electrode 13 moves forward, too. The rollable electrode 13 tends to roll or move forward when it contacts the tissues.

Figure 4:
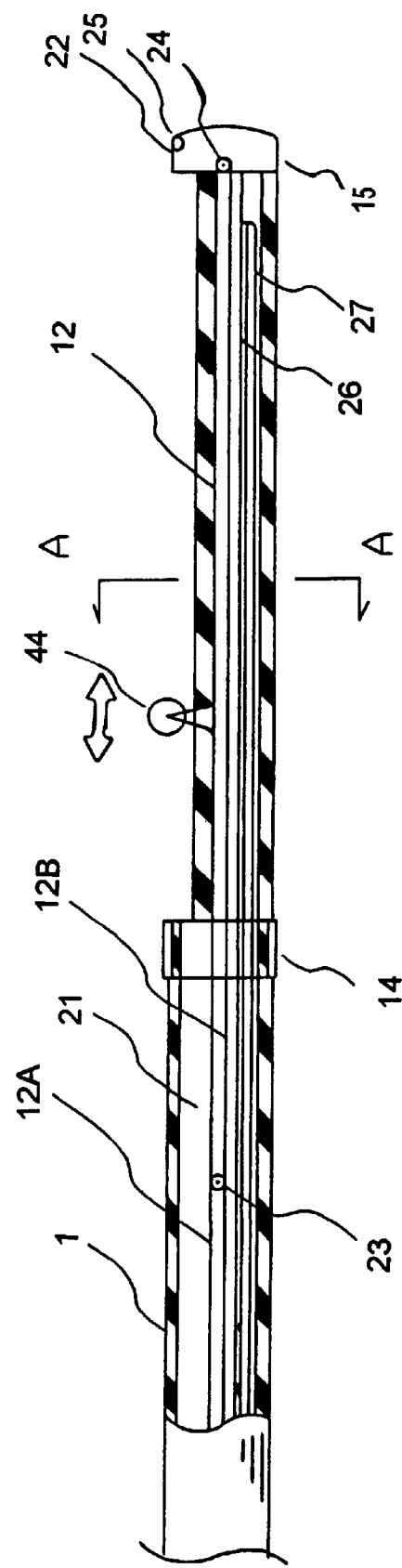
FIG. 4 is a cross-sectional view of the distal section of a catheter system comprising a movable electrode and its moving wire configuration.

FIG. 4 shows a cross-sectional view of the shaft distal section 2 of a catheter system comprising a first electrode 44 and its moving wire configuration 12. The electrode deployment means 11 and its associated moving wire 12 constitute the main mechanism of the electrode deployment capabilities. In one embodiment, the moving wire 12 is a close loop wiring and comprises a upper wire 12A and a lower wire 12B, which are supported by a first pulley 23 near the distal portion of the catheter shaft 1 and a second pulley 24 near the distal end of the catheter shaft 1. The electrode means, including a rollable electrode 44, a pair of electrode shafts 18, a plurality of supports 16, and anchoring leg means 19 are secured on the moving wire 12.

The second electrode 45 of the electrode means 13 has an insulated conducting wire (not shown) secured to the electrode, which passes through the lumen of the catheter shaft 1 and is soldered to a contact pin of the connector 8 at the proximal end of the handle 7. The returning conducting wire from the end of the connector is externally connected to a RF generator means during an electrophysiology ablation procedure. In principle, RF energy is delivered to the first electrode 44 through a first electrical conducting means 47, transmitted from the first electrode 44 to the second electrode 45 through the inflation fluid within the interior 43 of the inflated balloon 42, and returned from the second electrode 45 to said generator means through a second electrical conducting means 48 for generating heat inside the inflatable balloon 42.

The catheter system may further comprise at least one additional electrode 22 or 46 disposed at the shaft distal tip section 2 for electrophysiology study.

A temperature sensor 25, either a thermocouple means or a thermister means, is constructed at the proximity of the electrode 45 or 22 to measure the fluid temperature when RF energy is delivered. The temperature sensing wire (not shown) from the thermocouple or thermister is connected to one of the contact pins (not shown) of the connector 8 and externally connected to a transducer and to a temperature controller. The temperature reading is thereafter relayed to a closed-loop control mechanism to adjust the RF energy output. The RF energy delivered is thus controlled by the temperature sensor reading or by a pre-programmed control algorithm. The ablation catheter system further comprises a steering mechanism 9 at the handle 7 for controlling deflection of the said distal tip section 2. Usually a rotating ring or a push-pull plunger 8 is employed in the steering mechanism. A flat wire 26 is disposed at the distal tip section 2. A pulling wire 27 is used to control the degree of pulling on the flat wire 26, thus effecting the deflection of the catheter shaft 1 at the distal portion 2.

Figure 5:
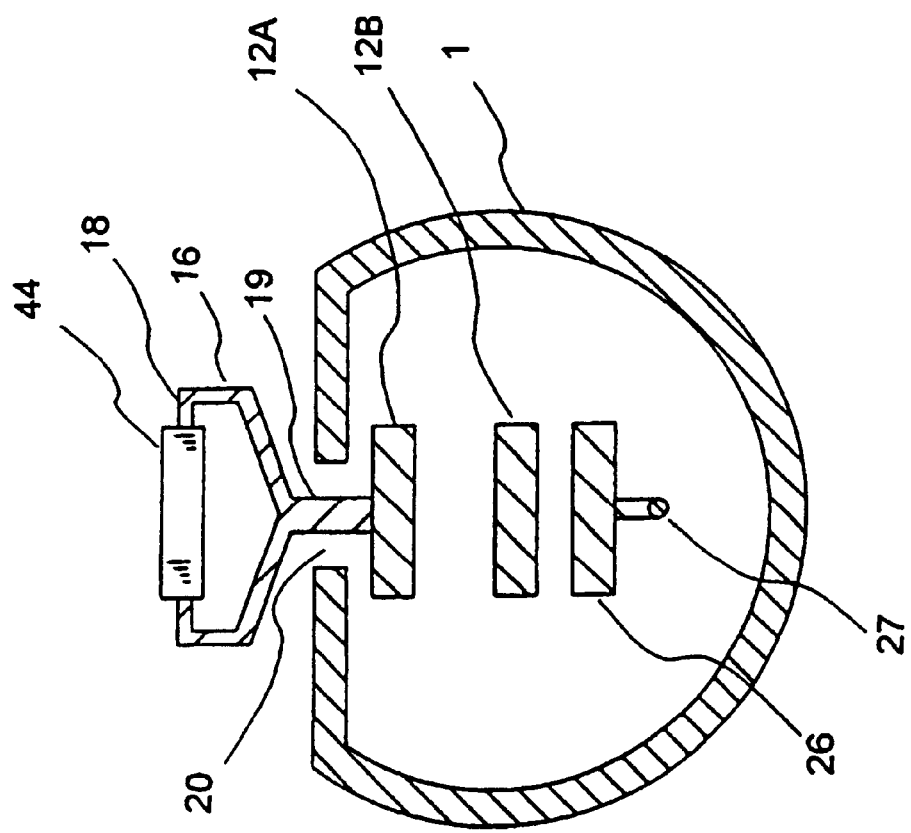
FIG. 5 is a transverse view of the attachment setup of a rollable electrode means on a moving wire inside the elongated open groove of a catheter shaft.

In a preferred embodiment, FIG. 5 shows a transverse view of the attachment setup of the rollable electrode on a moving wire 12 inside the open groove 17 of a catheter shaft 1. The electrode means 13 comprises a rollable electrode 44, electrode shafts 18, supports 16, and anchoring leg means 19. The anchoring leg means 19 is firmly secured on the upper moving wire 12A. The upper moving wire 12A and the returning lower moving wire 12B constitute a close-loop wiring, which is controlled by the electrode rolling controller 11 for moving the said wire forward or backward.

Figure 6:
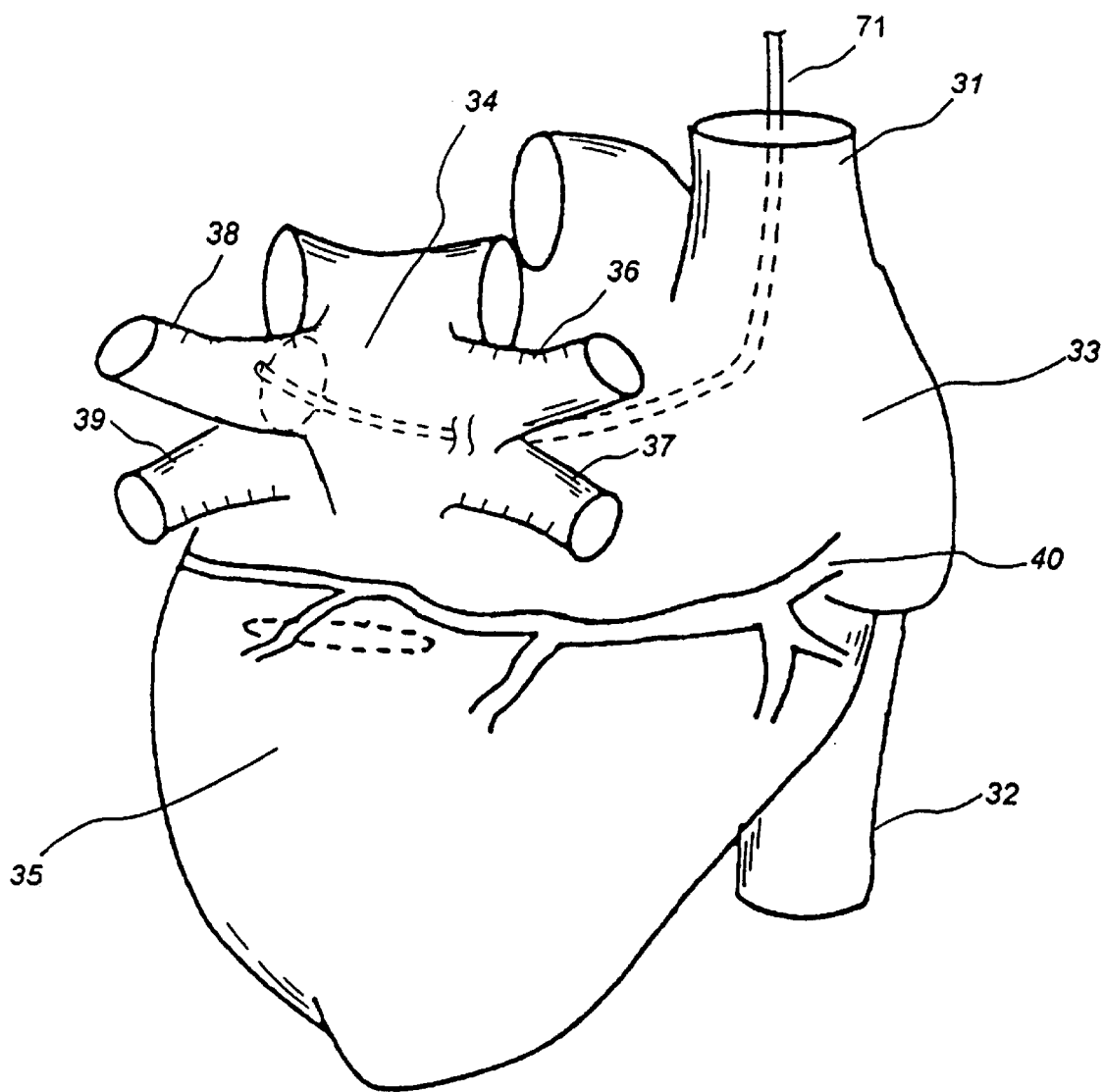
FIG. 6 is a simulated view of the catheter of the present invention in contact with the tissues.

FIG. 6 shows a perspective view of a catheter probe of the present invention when placed inside one pulmonary vein of the left atrium for paroxysmal atrial fibrillation treatment. To better illustrate the application of the present invention, a human heart is shown in FIG. 6. Blood returning from superior vena cava 31 or inferior vena cava 32 flows back to the right atrium 33. A coronary sinus 40 is part of the coronary artery system to provide nutrient to the epicardial heart tissue, wherein the heart also comprises a left atrium 34, a left ventricle 35 and a right ventricle. A catheter probe 71 of the present invention passing through the superior vena cava 31 into the right atrium 33. The catheter with a delivery sheath or a guiding catheter passes through the septum into the left atrium 34 for paroxysmal AFib treatment by using a standard trans-septal procedure. A normal person has four pulmonary veins: right superior pulmonary vein 36, right inferior pulmonary vein 37, left superior pulmonary vein 38, and left inferior pulmonary vein 39. In one example, a catheter probe 71 is inserted into the left atrium while its distal tip section is inserted into the left superior pulmonary vein 38. After the distal portion of the catheter probe 71 is inside the vein 38, the circular guidewire electrode 10 of the guidewire electrode means 9 is deployed either from said delivery sheath or from the outer catheter shaft as shown in the alternate preferred embodiment, FIG. 5. The deployed guidewire electrode is used for creating a continuous circular lesion inside or around the ostium of a pulmonary vein.

A method for operating a catheter system having a bipolar electrode pair enclosed within an inflatable balloon within a heart, the method comprises percutaneously introducing the catheter system through a blood vessel to the heart; positioning the shaft distal tip section on an interior wall of the heart; and applying RF energy to the bipolar electrode pair for tissue ablation, wherein RF energy is provided from an external RF energy generator means to the first electrode through a first electrical conducting means, transmitted from the first electrode to the second electrode, and returned from the second electrode to said generator means through a second electrical conducting means for generating heat inside the inflatable balloon.

From the foregoing, it should now be appreciated that an improved catheter system having a bipolar electrode pair means within an inflated balloon for heating the inflation fluid to cause circular lesion has been disclosed for ablation procedures, including endocardial, epicardial, or a pulmonary vein. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:
    a flexible catheter shaft having a shaft distal tip section, a shaft distal end, a shaft proximal end, and at least one lumen extending therebetween, the shaft distal tip section having an elongated open groove, wherein the at least one lumen comprises an inflation lumen;
    a handle attached to the shaft proximal end, wherein the handle has a cavity;
    an inflatable balloon mounted at the shaft distal tip section, wherein the inflation lumen opens into and is in communication with an interior of the inflatable balloon;
    an electrode means comprising a first movable electrode positioned at the elongated open groove and a second electrode to form a bipolar electrode pair, wherein the electrode means is mounted at the shaft distal tip section and is completely enclosed within the inflatable balloon; and
    an electrode deployment means mounted on the handle for longitudinally moving the first movable electrode of the electrode means back and forth along the elongated open groove.

2. The catheter system of claim 1, wherein the electrode means further comprising a support and an anchoring leg means disposed inside the elongated open groove for the movable electrode, wherein said movable electrode is positioned on the support and wherein the support is connected to the anchoring leg means which is then secured onto a moving wire means of the electrode deployment means.

3. The catheter system of claim 1, wherein the movable electrode is a rollable electrode.

4. The catheter system of claim 1, wherein the second electrode is positioned on a second support and wherein the second support is connected to a second anchoring leg means which is then secured onto said moving wire means of the electrode deployment means.

5. The catheter system of claim 1, wherein the inflatable balloon is made of a material selected from the group consisting of silicone, polyurethane, polyethylene, cross-linked polyethylene, conductive silicone, polyethylene terephthalate, latex, semipermeable membrane, and nylon.

6. The catheter system of claim 1, wherein a sodium chloride containing liquid is used to inflate the inflatable balloon.

7. The catheter system as in claim 1 further comprising a steering mechanism at the handle for controlling deflection of the shaft distal tip section of the catheter system.

8. The catheter system as in claim 1 further comprising at least one additional electrode disposed at the shaft distal tip section.

9. The catheter system as in claim 1 further comprising a RF energy generator means, wherein RF energy is delivered to the first electrode through a first electrical conducting means, transmitted from the first electrode to the second electrode, and returned from the second electrode to said generator means through a second electrical conducting means for generating heat inside the inflatable balloon.

10. The catheter system as in claim 9 further comprising a temperature sensing means at the shaft distal tip section for sensing a temperature.

11. The catheter system of claim 1, wherein the bipolar electrode pair is made of a material selected from the group consisting of platinum, iridium, gold, silver, stainless steel, and Nitinol.

12. A method for operating a catheter system having a bipolar electrode pair enclosed within an inflatable balloon within a heart, the catheter system comprising a flexible catheter shaft having a shaft distal tip section, a shaft distal end, a shaft proximal end, and at least one lumen extending therebetween, wherein the at least one lumen comprises an inflation lumen; a handle attached to the shaft proximal end; an inflatable balloon mounted at the shaft distal tip section, wherein the inflation lumen opens into and is in communication with an interior of the inflatable balloon; an electrode means comprising a first electrode and a second electrode to form a bipolar electrode pair, wherein the electrode means is mounted at the shaft distal tip section and is completely enclosed within the inflatable balloon, wherein a portion of the shaft distal tip section that is enclosed within the inflatable balloon comprises an elongated open groove, and wherein the first electrode is movable and is positioned at the elongated open groove for longitudinally moving the first electrode of the electrode means back and forth; and an electrode deployment means mounted on the handle; the method comprising:

(a) percutaneously introducing the catheter system through a blood vessel to the heart;

(b) positioning the shaft distal tip section on an interior wall of the heart; and (c) applying RF energy to the bipolar electrode pair for tissue ablation, wherein RF energy is provided from an external RF energy generator means to the first electrode through a first electrical conducting means, transmitted from the first electrode to the second electrode, and returned from the second electrode to said generator means through a second electrical conducting means for generating heat inside the inflatable balloon.

13. The method for operating a catheter system of claim 12, wherein the electrode means further comprises a support and an anchoring leg means disposed inside the elongated open groove for the first electrode, wherein said first electrode is positioned on the support and wherein the support is connected to the anchoring leg means which is then secured onto a moving wire means of the electrode deployment means.

* * * * *